United States Patent
Boss et al.

(10) Patent No.: US 12,409,181 B2
(45) Date of Patent: Sep. 9, 2025

(54) TREATMENT FOR AORTIC ANEURYSMS

(71) Applicant: THE REGENTS OF THE UNIVERSITY OF CALIFORNIA, Oakland, CA (US)

(72) Inventors: Gerard Boss, La Jolla, CA (US); Darren Casteel, La Jolla, CA (US); Hema Rangaswami, La Jolla, CA (US); Renate Pilz, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 904 days.

(21) Appl. No.: 17/616,122

(22) PCT Filed: Jun. 3, 2020

(86) PCT No.: PCT/US2020/035860
§ 371 (c)(1),
(2) Date: Dec. 2, 2021

(87) PCT Pub. No.: WO2020/247453
PCT Pub. Date: Dec. 10, 2020

(65) Prior Publication Data
US 2022/0305024 A1    Sep. 29, 2022

Related U.S. Application Data

(60) Provisional application No. 62/857,976, filed on Jun. 6, 2019.

(51) Int. Cl.
*A61K 31/555* (2006.01)
*A61P 9/00* (2006.01)

(52) U.S. Cl.
CPC .............. *A61K 31/555* (2013.01); *A61P 9/00* (2018.01)

(58) Field of Classification Search
CPC .................................................... A61K 31/555
USPC ........................................................... 514/184
See application file for complete search history.

(56) References Cited

U.S. PATENT DOCUMENTS

| | | | |
|---|---|---|---|
| 8,431,561 B2 * | 4/2013 | Boss | A61K 31/70 514/52 |
| 9,402,826 B2 | 8/2016 | Ambron et al. | |
| 2008/0227746 A1 | 9/2008 | Boss et al. | |
| 2013/0011922 A1 | 1/2013 | Quay et al. | |
| 2015/0359832 A1 | 12/2015 | Elmann et al. | |
| 2017/0151202 A1 | 6/2017 | Mason | |

FOREIGN PATENT DOCUMENTS

WO    2019006384 A1    1/2019

OTHER PUBLICATIONS

Anantharam et al., Cobinamide is Effective for Treatment of Hydrogen Sulfide-Induced Neurological Sequelae in a Mouse Model, Ann. NY, Acad Sci, vol. 1408, 2017, Pags 61-78.
International Search Report and the Written Opinion for International Application No. PCT/US2020/035860, mailed Aug. 24, 2020.

* cited by examiner

*Primary Examiner* — Kahsay Habte
(74) *Attorney, Agent, or Firm* — Eversheds-Sutherland (US) LLP

(57) ABSTRACT

Compositions and methods for treatment of aortic disease in a subject in need comprising an effective amount of cobinamide. Aortic diseases include for example aortic aneurysm, aortic dissection, or aortic dilation. Aortic disease can be caused for example by Marfan syndrome or oxidative stress.

12 Claims, 5 Drawing Sheets

TREATMENT FOR AORTIC ANEURYSMS

CROSS REFERENCE TO RELATED APPLICATIONS

This application is a U.S. National Phase Application of PCT Application No. PCT/US2020/035860, filed on Jun. 3, 2020, which claims priority benefit to U.S. Provisional Application No. 62/857,976, filed Jun. 6, 2019, the entire contents of which are incorporated herein by reference.

GOVERNMENT SPONSORSHIP

This invention was made with government support under grants No. HL132141, NS058030, and NS087964 awarded by the National Institutes of Health. The government has certain rights in the invention.

TECHNICAL FIELD

The present invention relates to a treatment for aortic aneurysms.

BACKGROUND

Aortic aneurysms account for 1-2% of deaths in Western countries, and despite improvements in surgical repair, morbidity and mortality remain high, especially with thoracic aortic aneurysms and dissections (TAAD).[4, 5] Blood pressure control with β-adrenergic or angiotensin receptor blockers modestly improves prognosis.[4-6] The thoracic aortic pathology in TAAD is characterized by progressive elastin fiber fragmentation, smooth muscle cell (SMC) loss, and collagen accumulation, leading to aortic dilation and/or rupture.[5] Mutations causing hereditary TAAD affect proteins regulating transforming growth factor-β (TGF-β) signalling, e.g., TGF-β receptors-1 and -2 in Loeys-Dietz syndrome and fibrillin-1 in Marfan syndrome, or components of the SMC contractile apparatus, e.g., SM-α-actin (ACTA2) and myosin heavy chain-11 (MYH11).[5, 7] Aortic pathology has been attributed to SMC dedifferentiation and activation of stress pathways leading to increased production of tissue-destructive matrix metalloproteinases (MMPs).[5, 8-12]

Protein kinase G1 (PKG1, gene name PRKG1) mediates vasodilation in response to nitric oxide (NO)-induced cGMP synthesis.[3, 13] It also regulates SMC differentiation, preventing a de-differentiated, proliferative phenotype after vascular injury.[14-17] Excess NO may contribute to aortic disease in Marfan syndrome and other forms of TAAD, but whether NO's effects are mediated by PKG is unknown.[18] Case reports suggest that long-term use of PKG-activating drugs, e.g., phosphodiesterase-5 inhibitors for erectile dysfunction or pulmonary hypertension, may increase risk for acute aortic dissections.[19-23] It was also previously identified that a recurrent gain-of-function mutation in PRKG1 is a cause of early-onset thoracic aortic disease in humans.[1]

SUMMARY OF THE INVENTION

In embodiments, the invention provides a method of treating aortic disease in a subject comprising administering to a subject in need an effective amount of cobinamide, a cobinamide derivative, or a salt thereof.

In embodiments, the invention provides a method of treating aortic disease wherein the aortic disease is aortic aneurysm, aortic dissection, or aortic dilation.

In embodiments, the invention provides a method of treating aortic disease wherein the aortic disease is due to Marfan syndrome.

In embodiments, a cobalt atom of the cobinamide, cobinamide derivative, or salt thereof independently may be coordinated with one or more ligands.

In embodiments, the cobinamide, cobinamide derivative, or salt thereof is administered orally.

In embodiments, the invention provides a method of treating oxidative stress disease in a subject comprising administering to a subject in need an effective amount of cobinamide, a cobinamide derivative, or a salt thereof.

In embodiments, the oxidative stress disease causes an aortic aneurysm, aortic dissection, or aortic dilation.

In embodiments, the oxidative stress disease is due to Marfan syndrome.

In embodiments, the invention provides for a method of treating aortic disease comprising administering to a subject in need an effective amount of a composition comprising an anti-oxidant to lower reactive oxygen species.

In embodiments, the anti-oxidant is cobinamide, a cobinamide derivative, or a salt thereof.

In embodiments, the composition inhibits aortic dilation and SMC loss.

In embodiments, the composition inhibits elastin fiber breaks.

In embodiments, the composition inhibits $H_2O_2$-induced JNK activation and protein oxidation.

In embodiments, the composition downregulates Hif-1α/Vegfa or Tgfb1/Ctgf pathways.

In embodiments, the composition inhibits PKG activity.

BRIEF DESCRIPTION OF THE DRAWINGS

FIGS. 1A-1J show mice heterozygous for the Prkg1$^{RQ}$ mutation develop age-related pathologic changes in the thoracic aortic. FIGS. 1A-1B show PKG activity was measured in aortic extracts from wild type (WT) and Prkg1$^{RQ/+}$ mice by an in vitro kinase assay using a synthetic peptide (a, n=2 M+6 F mice per genotype) or by assessing phosphorylation of vasodilator-stimulated protein (VASP) using a phospho-Ser$^{239}$-specific antibody (b, n=5 M+6 F mice per genotype). The PKG inhibitor DT was added to extracts as indicated. PKG expression and VASP phosphorylation in aortas from three wild type and three mutant mice are shown in the Western blot. FIGS. 1C-1D show systolic blood pressure measured by telemetry over 24 h in 4-month-old WT and Prkg1$^{RQ/+}$ mice (n=4 male mice per genotype), and mean arterial pressure (MAP) averaged separately during rest (7 am-7 pm) and activity (7 pm-7 am). In FIGS. 1G and 1H n=5 M+5 F mice and in FIGS. 1I and 1J n=3 M+3-4 F per genotype. *p<0.05, p<0.01, *p<0.001 for the indicated comparisons by two-sided Student's t-test (FIGS. 1B, 1F, 1H, 1I and 1J), Mann-Whitney test (FIG. 1G), or two-way ANOVA (FIGS. 1A and 1D; #p<0.05 for comparison of basal activity in WT versus RQ/+; +p<0.05 and +++p<0.001 for comparison of the same condition in the absence versus presence of DT2). In FIGS. 1G and 1H, ns=non-significant.

FIGS. 2A-2J show contractile genes, TGF-β-related genes, and Nox4 are upregulated, and oxidative stress and MMP activity are increased in aortas of Prkg1$^{RQ/+}$ mice. In FIG. 2D, arrows point to examples of brown nuclei counted as positive; scale bar 50 μm, n=2 M+3 F mice per genotype). Lipid peroxidation was assessed by measuring aorta malondialdehyde (MDA) content using thiobarbituric acid (FIG. 2E, n=2 M+5 F mice). Ascorbyl radical was measured in serum by electron paramagnetic resonance (FIG. 2F, n=2 M+5 F mice). Protein carbonyl groups were detected by OxyBlot™ after derivatization of aortic extracts with 2,4-dinitrophenylhydrazine (DNPH); non-derivatized extracts served as control and reprobing with a β-actin antibody showed equal loading (FIG. 2G, ImageJ quantification for n=2 M+2 F mice per genotype below).

FIGS. 3A-3O show PKG$^{RQ}$ expression in human aortic SMCs recapitulates pathological changes in the aorta of Prkg1$^{RQ/+}$ mice, with Nox4 upregulation leading to increased oxidative stress and apoptosis, and reduced proliferation. Human aortic SMCs were infected with adenovirus encoding green fluorescent protein (control), wild type PKG1 (PKG1$^{WT}$), PKG1$^{RQ}$, or NOX4, as indicated.

FIGS. 4A-4G show cobinamide reduces oxidative stress and prevents development of thoracic aortic abnormalities in aging PKG$^{RQ/+}$ mice. Starting at 6 months of age, wild type (WT, n=5 M+4 F mice) and Prkg1$^{RQ/+}$ mice (RQ/+, n=5 M+7 F mice) received 1 mM histidyl-cobinamide (Cbi) in the drinking water for 6 months; controls were left untreated (WT n=7 M+7 F, and RQ/+n=9 M+11 F mice). All mice were analysed by ultrasound (FIG. 4D); at least five mice per group (both genders) were analysed in the other panels.

FIGS. 5A-5J show transverse aortic constriction (TAC) induces severe aortic pathology and death from aortic rupture in young Prkg1$^{RQ/+}$ mice, and the effect of NAC. FIG. 5J shows schema summarizing consequences of mutant PKG1$^{RQ}$ expression in the aorta. Constitutive activation of PKG1 activates JNK and causes increased $H_2O_2$ production from NOX4 up-regulation; oxidative stress further enhances JNK activation, directly activates MMPs and upregulates MMPs via JNK activation, and MMPs degrade elastin fibers. Constitutive PKG1 activation causes SMC loss from decreased proliferation and increased SMC apoptosis; these effects are in part JNK mediated and enhanced by oxidative stress. Constitutive PKG1 activation increases expression of contractile proteins, HIF-1α/VEGF, and TGF-β/TGF-β target genes; the latter promote aortic media fibrosis, which may be compensatory. Aortic media degeneration leads to age-dependent aortic dilation, and aortic dissections under hypertensive stress. Cobinamide (Cbi) or N-acetylcysteine (NAC) treatment reduce oxidative stress and JNK activation, preserving aortic media integrity.

DETAILED DESCRIPTION

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, 2$^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, 20$^{th}$ ed., (Lippincott, Williams & Wilkins 2003), and Remington, The Science and Practice of Pharmacy, 22$^{th}$ ed., (Pharmaceutical Press and Philadelphia College of Pharmacy at University of the Sciences 2012).

As used herein, the terms "comprises," "comprising," "includes," "including," "has," "having," "contains", "containing," "characterized by," or any other variation thereof, are intended to encompass a non-exclusive inclusion, subject to any limitation explicitly indicated otherwise, of the recited components. For example, a pharmaceutical composition, and/or a method that "comprises" a list of elements (e.g., components, features, or steps) is not necessarily limited to only those elements (or components or steps), but may include other elements (or components or steps) not expressly listed or inherent to the pharmaceutical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a fusion protein, pharmaceutical composition, and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

It is understood that aspects and embodiments of the invention described herein include "consisting" and/or "consisting essentially of" aspects and embodiments.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Values or ranges may be also be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

As used herein, "patient" or "subject" means a human or mammalian animal subject to be treated.

As used herein the term "pharmaceutical composition" refers to a pharmaceutical acceptable composition, wherein the composition comprises a pharmaceutically active agent, and in some embodiments further comprises a pharmaceutically acceptable carrier. In some embodiments, the pharmaceutical composition may be a combination of pharmaceutically active agents and carriers.

The term "combination" refers to either a fixed combination in one dosage unit form, or a kit of parts for the combined administration where one or more active compounds and a combination partner (e.g., another drug as explained below, also referred to as "therapeutic agent" or "co-agent") may be administered independently at the same time or separately within time intervals. In some circumstances, the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein the term "pharmaceutically acceptable" means approved by a regulatory agency of the Federal or a state government or listed in the U.S. Pharmacopoeia, other generally recognized pharmacopoeia in addition to other formulations that are safe for use in subjects, such as animals, and more particularly in humans and/or non-human mammals.

As used herein the term "pharmaceutically acceptable carrier" refers to an excipient, diluent, preservative, solubilizer, emulsifier, adjuvant, and/or vehicle with which a pharmaceutically active compound, such as a cobinamide compound, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

As used herein, "therapeutically effective" refers to an amount of a pharmaceutically active compound(s) that is sufficient to treat or ameliorate, or in some manner reduce the symptoms associated with diseases and medical conditions. When used with reference to a method, the method is sufficiently effective to treat or ameliorate, or in some manner reduce the symptoms associated with diseases or conditions. For example, an effective amount in reference to diseases is that amount which is sufficient to block or prevent onset; or if disease pathology has begun, to palliate, ameliorate, stabilize, reverse or slow progression of the disease, or otherwise reduce pathological consequences of the disease. In any case, an effective amount may be given in single or divided doses.

In some embodiments a "therapeutically effective amount" refers to an amount of one or more compounds, such as but not limited to cobinamide, that is sufficient to treat or ameliorate, or in some manner reduce the symptoms associated with aortic diseases.

As used herein, the terms "treat," "treatment," or "treating" embraces at least an amelioration of the symptoms associated with diseases in the patient, where amelioration is used in a broad sense to refer to at least a reduction in the magnitude of a parameter, e.g. a symptom associated with the disease or condition being treated. As such, "treatment" also includes situations where the disease, disorder, or pathological condition, or at least symptoms associated therewith, are completely inhibited (e.g. prevented from happening) or stopped (e.g. terminated) such that the patient no longer suffers from the condition, or at least the symptoms that characterize the condition.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. In certain embodiments, subjects with familial history of a disease are potential candidates for preventive regimens. In certain embodiments, subjects who have a history of recurring symptoms are also potential candidates for prevention. In this regard, the term "prevention" may be interchangeably used with the term "prophylactic treatment."

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, a compound described herein is intended to encompass all possible stereoisomers, unless a particular stereochemistry is specified. Where structural isomers of a compound are interconvertible via a low energy barrier, the compound may exist as a single tautomer or a mixture of tautomers. This can take the form of proton tautomerism; or so-called valence tautomerism in the compound, e.g., that contain an aromatic moiety.

The invention contemplates the use of cobinamide and cobinamide derivatives. A cobalt atom of the cobinamide and cobinamide derivatives independently may be coordinated with no ligands or one or more ligands, for example, one ligand or two ligands. As used herein, the phrase "cobinamide derivative" refers to a biologically active derivative (e.g., analog) of cobinamide, such as a heterocyclic or heteropolycyclic compound that is (i) coordinated with a central cobalt atom, and (ii) substituted with two or more alkyl substituents (e.g., four to eight alkyl substituents) that include at least one polar functional group, such as an amide, an ester, an ether, carboxylic acid, etc. The heterocyclic or heteropolycyclic compound may include 4 heteroatoms, such as nitrogen, oxygen, etc. The one or more ligands may include any ligand that is capable of coordinating with a cobalt atom, such as an unsubstituted or substituted tetrazole (e.g., an amino-tetrazole, an acetyl-tetrazole, etc.), an unsubstituted or substituted imidazole (e.g., acetyl-imidazole), histidine, etc. An exemplary cobinamide derivative is trihistidylcobinamide. As used herein, the phrase "amino-tetrazole" refers to a tetrazole moiety substituted at any one or more positions with (i) an amino moiety and/or (ii) a $C_1$-$C_3$ alkyl comprising an amino moiety. As used herein, the phrase "acetyl-tetrazole" refers to a tetrazole moiety substituted at any one or more positions with (i) an acetyl moiety and/or (ii) a $C_1$-$C_3$ alkyl comprising an acetyl moiety. As used herein, the phrase "acetyl-imidazole" refers to an imidazole moiety that is substituted at any one or more positions with (i) an acetyl moiety and/or (ii) a $C_1$-$C_3$ alkyl comprising an acetyl moiety.

In some embodiments, the one or more cobinamide derivative include an amino-tetrazole-cobinamide, a di-(amino-tetrazole)-cobinamide, an acetyl-tetrazole-cobinamide, a di-(acetyl-tetrazole)-cobinamide, an acetyl-imidazole-cobinamide, a di-(acetyl-imidazole)-cobinamide, or a combination thereof. An example of an amino-tetrazole-cobinamide is 5-amino-tetrazole-cobinamide. An example of a di-(amino-tetrazole)-cobinamide is di-(5-amino-tetrazole)-cobinamide. An example of an acetyl-tetrazole-cobinamide is 5-acetyl-tetrazole-cobinamide. An example of a di-(acetyl-tetrazole)-cobinamide is di-(5-acetyl-tetrazole)-cobinamide. An example of an acetyl-imidazole-cobinamide is 4-acetyl-imidazole-cobinamide. An example of a di-(acetyl-imidazole)-cobinamide is di-(4-acetyl-imidazole)-cobinamide.

The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

The term "pharmaceutically acceptable salt" as used herein refers to acid addition salts or base addition salts of the compounds, such as the multi-drug conjugates, in the present disclosure. A pharmaceutically acceptable salt is any salt which retains the activity of the parent agent or compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66: 1, 1977). In some embodiments, a "pharmaceutically acceptable salt" is intended to mean a salt of a free acid or base of an agent or compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. An agent or compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, [gamma]-hydroxybutyrates, glycolates, tartrates, and mandelates.

In embodiments, the invention provides a method of treating aortic disease in a subject comprising administering to a subject in need an effective amount of cobinamide, a cobinamide derivative, or a salt thereof. In embodiments, the aortic disease is aortic (e.g., aortic arch, ascending thoracic, descending thoracic, or abdominal) aneurysm, aortic dissection, or aortic dilation. In embodiments, the aortic disease is due to Marfan syndrome or thoracic aortic aneurysms and dissections (TAAD). In embodiments, the aortic disease is due to a genetic or non-heritable condition leading to aortic aneurysm.

In embodiments, the invention provides that a cobalt atom of the cobinamide, cobinamide derivative, or salt thereof independently may be coordinated with one or more ligands.

In embodiments, the cobinamide, cobinamide derivative, or salt thereof is administered orally. The route of administration may be oral, nasal, buccal, parenteral administration such as intravenous administration, intramuscular administration, subcutaneous administration, dermal administration, or direct administration to the target organ or tissue.

In embodiments, the invention provides a method of treating oxidative stress disease in a subject comprising administering to a subject in need an effective amount of cobinamide, a cobinamide derivative, or a salt thereof. In embodiments, the oxidative stress disease causes an aortic aneurysm, aortic dissection, or aortic dilation. In embodiments, the oxidative stress disease is due to Marfan syndrome or thoracic aortic aneurysms and dissections (TAAD). In embodiments, the aortic disease is due to a genetic or non-heritable condition leading to aortic aneurysm.

In embodiments, the invention provides for a method of treating aortic disease comprising administering to a subject in need an effective amount of a composition comprising an anti-oxidant to lower reactive oxygen species. In embodiments, the anti-oxidant is cobinamide, a cobinamide derivative, or a salt thereof. In embodiments, the method inhibits aortic dilation and SMC loss. In embodiments, the method inhibits elastin fiber breaks. In embodiments, the method inhibits $H_2O_2$-induced JNK activation and protein oxidation. In embodiments, the method downregulates Hif-1α/Vegfa or Tgfb1/Ctgf pathways. In embodiments, the method inhibits PKG activity.

In embodiments, pharmaceutical compositions are provided for use in the various methods described herein that comprises one or more cobinamide, a cobinamide derivative, or a salt thereof, and are formulated for delivery to a subject, wherein the pharmaceutical compositions are effective for treating an aortic disease state.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

To investigate mechanisms leading to TAAD in patients heterozygous for the PRKG1,p.Arg177Gln mutation, knock-in mice were generated carrying the mutation.[13] The mutation is located in the first cGMP-binding domain of the kinase and causes constitutive activation of both PKGIα and 1p isoforms. The catalytic domain is unchanged, and the mutant protein (hereafter referred to as PKG1$^{RQ}$) is still inhibited by the PKG-specific peptide DT2.[24] About 50% of homozygous mice (referred to as Prgk$^{RQ/RQ}$) died within the first six weeks of life from gastro-intestinal dysfunction, with dilated esophagus, stomach, and bowel. Surviving Prkg1$^{RQ/RQ}$ mice were underweight and smaller compared to wild type (WT) littermates, even when given liquid food after weaning. Heterozygous Prkg1$^{RQ/+}$ mice were the focus, because heterozygous humans manifest disease. Prkg1$^{RQ/+}$ mice appeared healthy, weighed the same as WT littermates, and had no obvious developmental abnormalities of the aorta.

Figure 1A:
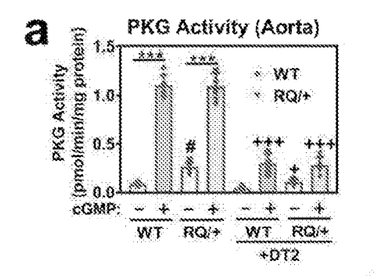
Figure 1B:
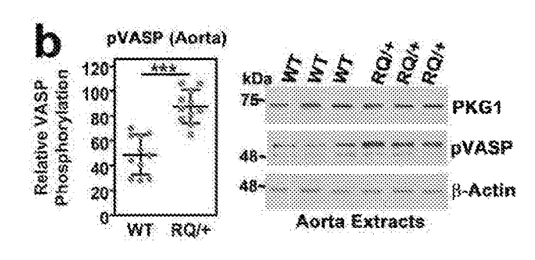

PKG1 protein and cGMP-stimulated PKG activity were the same in aortas from Prkg1$^{RQ/+}$ mice and their WT littermates, but basal PKG activity in the absence of cGMP was three-fold higher in aortas from mutant mice, when measured with a peptide substrate (FIG. 1A) or by assessing phosphorylation of vasodilator-stimulated phosphoprotein (pVASP, FIG. 1B). Although the purified mutant enzyme is fully active in the absence of cGMP, basal PKG activity in heterozygous aortas was <50% of total, cGMP-stimulated activity (FIG. 1A), likely because the wild type enzyme inhibits the mutant enzyme in a heterodimer.[1] Similar to the purified enzyme, basal and cGMP-stimulated PKG activities in the aorta were largely inhibited by DT2 (FIG. 1A).

Figure 1C:
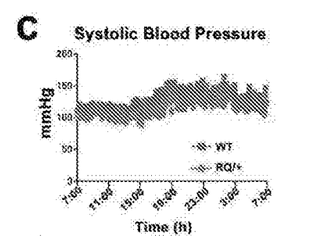
Figure 1D:
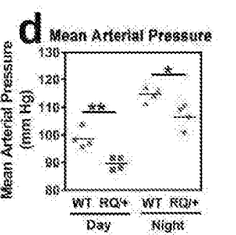

Humans carrying the PRKG1$^{R177Q}$ mutation are generally normotensive,[1] and consistent with this finding, Prkg1$^{RQ/+}$ mice had only modestly reduced systolic and diastolic blood pressures compared to wild type litter mates, resulting in ~10 mm Hg lower mean arterial pressures during sleep and wake hours (FIG. 1C,1D). Heart rate and pulse pressure were not altered. Thus, although acute PKG1 activation by NO/cGMP causes vasodilation and hypotension in mice and humans,[13] a sustained increase in basal PKG1 activity has a small effect on blood pressure.

The physiologic consequences of the PKG1$^{RQ}$ mutant protein were evaluated by assessing contraction of aortic rings derived from mutant and wild type mice. The concentration of prostaglandin F2α required to pre-contract rings was similar in aortas from eight month-old wild type and mutant mice (2.15±0.17 versus 2.27±0.86 µM; n=5 wild type and mutant vessels, respectively). However, relaxation of the rings in response to 8-CPT-cGMP or to acetylcholine—which is largely NO-mediated[25]—was reduced in the mutant mice compared to wild type mice. These data are consistent with higher basal, cGMP-independent PKG activity in the aortas of heterozygous mice compared to wild type mice, resulting in smaller cGMP-induced increases in enzyme activity. Reduced NO bioavailability due to oxidative stress in the Prkg1$^{RQ/+}$ mice (described below) may contribute to decreased acetylcholine-induced aortic relaxation, but this requires further investigation.

Figure 1E:
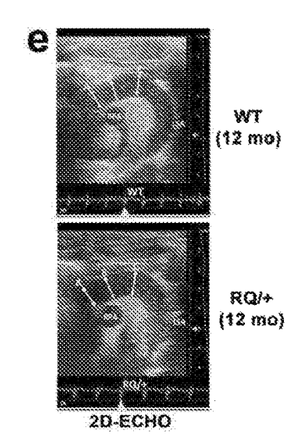
FIG. 1E shows ultrasound images of the thoracic aorta of 12-month-old WT and Prkg1$^{RQ/+}$ mice. Measurements were performed at end-diastole, indicated by an arrowhead below the ECG (A=aortic root; B=ascending aorta, and C=aortic arch; RPA, right pulmonary artery; LSA, left subclavian artery).
Figure 1F:
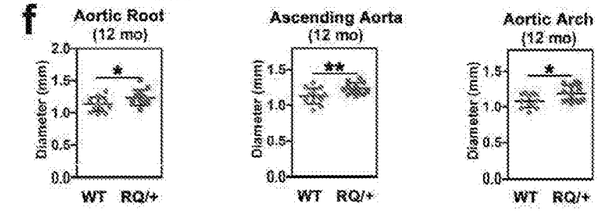
FIG. 1F shows a diameter of the aortic root, ascending aorta, and aortic arch measured by ultrasound in 12-month-old WT and Prkg1$^{RQ/+}$ mice (n=6 M+7 F mice per genotype).
Figure 1G:
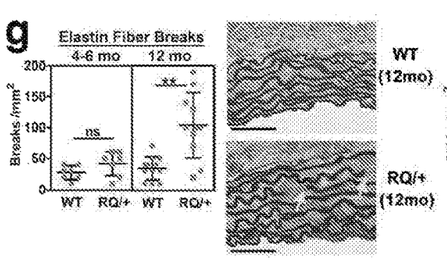
FIGS. 1G-1J show elastin fiber breaks (FIG. 1G), SMC density (FIG. 1H), SMC apoptosis (FIG. 1I), and media collagen content (FIG. 1J) of ascending aorta cross-sections from the animals assessed by Van Gieson's (FIG. 1G), hematoxylin/eosin (FIG. 1H), TUNEL (FIG. 1I), and Masson-Trichrome (FIG. 1J) stains (80× with 25 μm scale bars in FIGS. 1H and 1I and 40× with 50 μm bars in FIGS. 1G and 1J). Arrows in FIGS. 1G and 1I point to elastin fiber breaks and some TUNEL-positive brown nuclei, respectively. Collagen content (FIG. 1J, blue greyscales) of aortic media was quantified using ImagePro (A=adventitia; excluded).
Figure 1H:
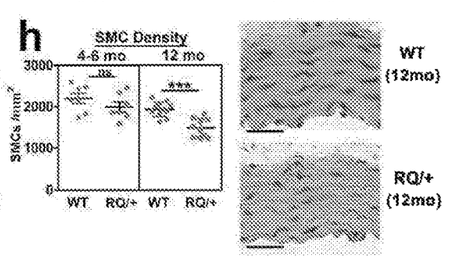
Figure 1I:
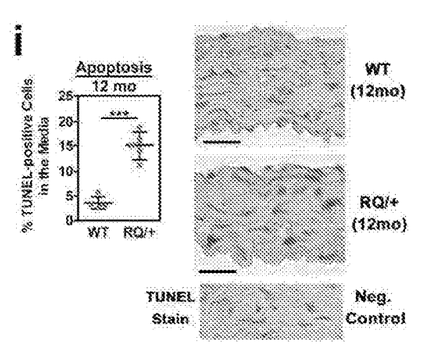
Figure 1J:
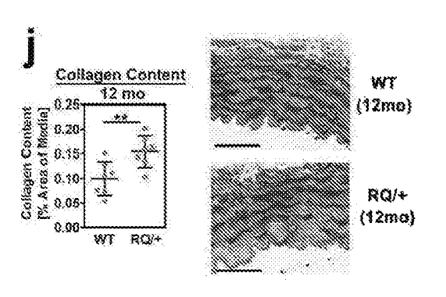

The Prkg1$^{RQ/+}$ mice had normal thoracic aorta dimensions at 4-6 months of age, but aortic dilation became apparent at 12 months, with similar phenotypic changes in males and females (FIGS. 1E,1F). While the aortas of young Prkg1$^{RQ/+}$ mice were histologically normal, the aortas of 12-month-old mutant mice had increased elastin fiber breaks, SMC apoptosis and loss of SMCs, and collagen accumulation in the media layer; media thickness was similar as in WT mice (FIGS. 1G-1J). Thus, aging Prkg1$^{RQ/+}$ mice recapitulated aortic changes observed in patients heterozygous for the PKG$^{RQ}$ mutation.[1,2]

Figure 2A:
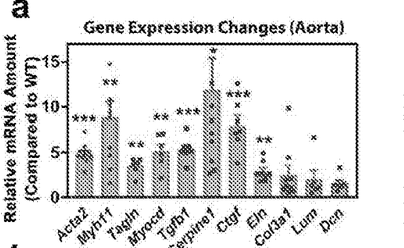
FIGS. 2A-2B show relative mRNA expression in aortas of 4-month-old PKG1$^{RQ/+}$ mice compared to wild type mice: smooth muscle α2-actin (Acta2); myosin heavy chain-11 (Myh11); transgelin (Tagln); myocardin (Myocd); TGF-β1 (Tgfb1); plasminogen activator inhibitor-1 (Serpine1); connective tissue growth factor (Ctgf); collagen3-α1 (Col3a1); elastin (Eln); lumican (Lum); decorin (Dcn); and NADPH oxidase-2 and -4 (Nox2, Nox4). Genes of interest were normalized to 18S rRNA and the mean ΔCt of WT mice was assigned a value of one (n=3-4 M+3-4 F mice per genotype).
Figure 2B:
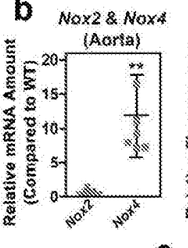
Figure 2C:
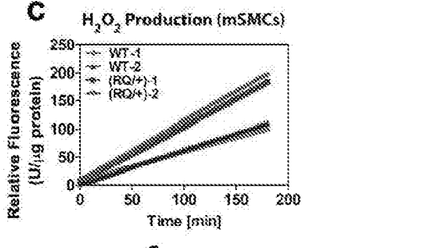
FIG. 2C shows $H_2O_2$ production of aortic SMCs isolated from WT and PKG$^{RQ/+}$ mice measured over time by Amplex Red fluorescence.
Figure 2D:
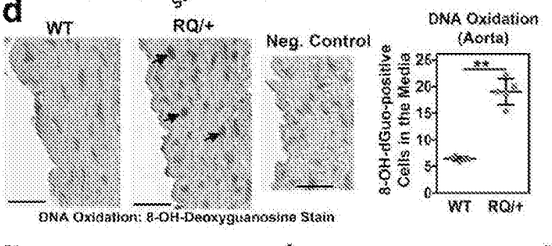
FIGS. 2D-2G show oxidative stress markers measured in aorta and serum of 8- to 12-month-old WT and PKG$^{RQ/+}$ mice. DNA oxidation was assessed by immunohistochemical staining of 8-OH-deoxyguanosine.
Figure 2E:
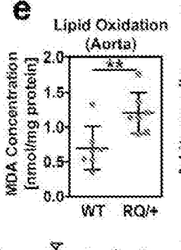
Figure 2F:
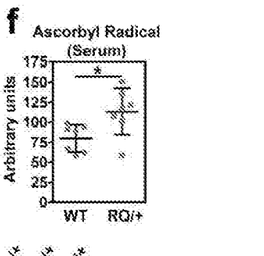
Figure 2G:
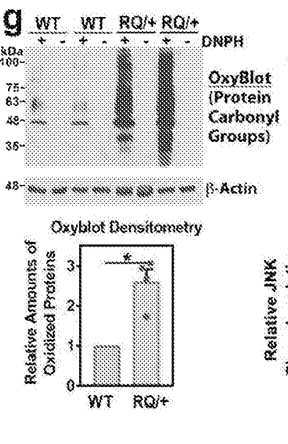

Compared to WT littermates, aortas from 4-month-old Prkg1$^{RQ/+}$ mice showed increased mRNAs encoding the SMC contractile proteins Acta2, Myh11, and Tagln, and the transcription factor myocardin, consistent with previous in vitro findings that PKG1 promotes a differentiated, contractile SMC phenotype (FIG. 2A).[14-16] Expression of TGFβ1 and its target genes Ctgf, Serpine1, Eln, and Nox4 were also increased in the mutant mice, while Col3a1 showed a modest non-significant increase; expression of the proteoglycans lumican (Lum), and decorin (Dcn) was unchanged (FIGS. 2A,2B). Increased TGF-β signalling occurs in other heritable diseases with TAAD, including Marfan syndrome.[12, 26, 27] However, the basis of increased TGF-β signalling, and whether it has a causative or compensatory role remains a matter of debate.[5, 5, 6, 12, 28]

Figure 2H:
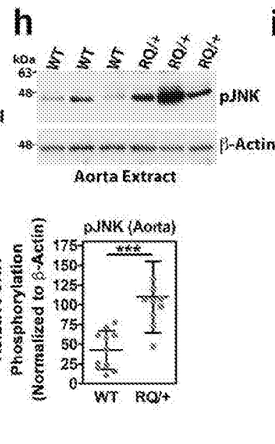
FIG. 2H shows JNK activation was assessed on Western blots of aortic extracts using a phospho-specific antibody, and was normalized to β-actin (ImageJ quantification for n=4 M+6 F mice per genotype below).
Figure 2I:
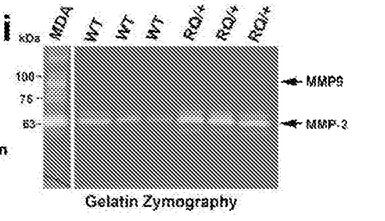
FIGS. 2I-2J show metalloproteinase (MMP) activity was assessed in aortic extracts by gelatin zymography (FIG. 2I, n=1 M+2 F mice per genotype) and measured using fluorescently-labelled elastin as a substrate (FIG. 2J, n=2 M+4 F mice per genotype; conditioned medium from MDA-MB231 cells served as positive control). *p<0.05, p<0.01, *p<0.001 for the indicated comparisons by one-sample t-test (FIGS. 2A, 2B and 2G), two-sided t-test (FIGS. 2E, 2F, 2H and 2J), or Mann-Whitney test (FIG. 2D).
Figure 2J:
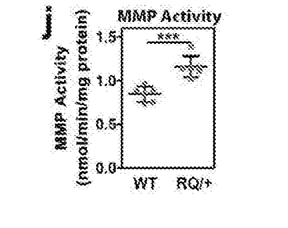

NADPH oxidase-4 (Nox4) mRNA was ~10-fold higher in aortas from Prkg1$^{RQ/+}$ compared to WT mice, but Nox2 was not altered and Nox1 was below detection (FIG. 2B). Nox4 is regulated primarily at the transcriptional level; the enzyme is constitutively active and generates mainly hydrogen peroxide ($H_2O_2$), with some superoxide ($O_2^-$).[29] SMCs isolated from Prkg1$^{RQ/+}$ aortas produced more $H_2O_2$ than those from WT aortas, and aortas from Prkg1$^{RQ/+}$ mice showed increased oxidative stress, evident by increased dihydroethidium staining and DNA-, lipid-, and protein-oxidation products; Prkg1$^{RQ/+}$ mice additionally had higher serum ascorbyl radical concentrations than WT mice (FIGS. 2C-2G). c-Jun N-terminal kinase (JNK) appears important in the pathogenesis of TAAD, because JNK up-regulates MMPs and induces SMC apoptosis, and JNK inhibitors reduce aortic aneurysms in Marfan mice and in other mouse models of TAAD.[10, 30-32] Increased activity of both JNK and MMPs in Prkg1$^{RQ/+}$ was found compared to WT aortas (FIGS. 2H-2J), consistent with JNK activation by $H_2O_2$ and via MEKK1 activation by PKG1.[30, 32-34]

Figures 3A, 3B, 3C, 3D, 3E, 3F, 3G, 3H, 3I, 3J, 3K, 3L, 3M, 3N, 3O:
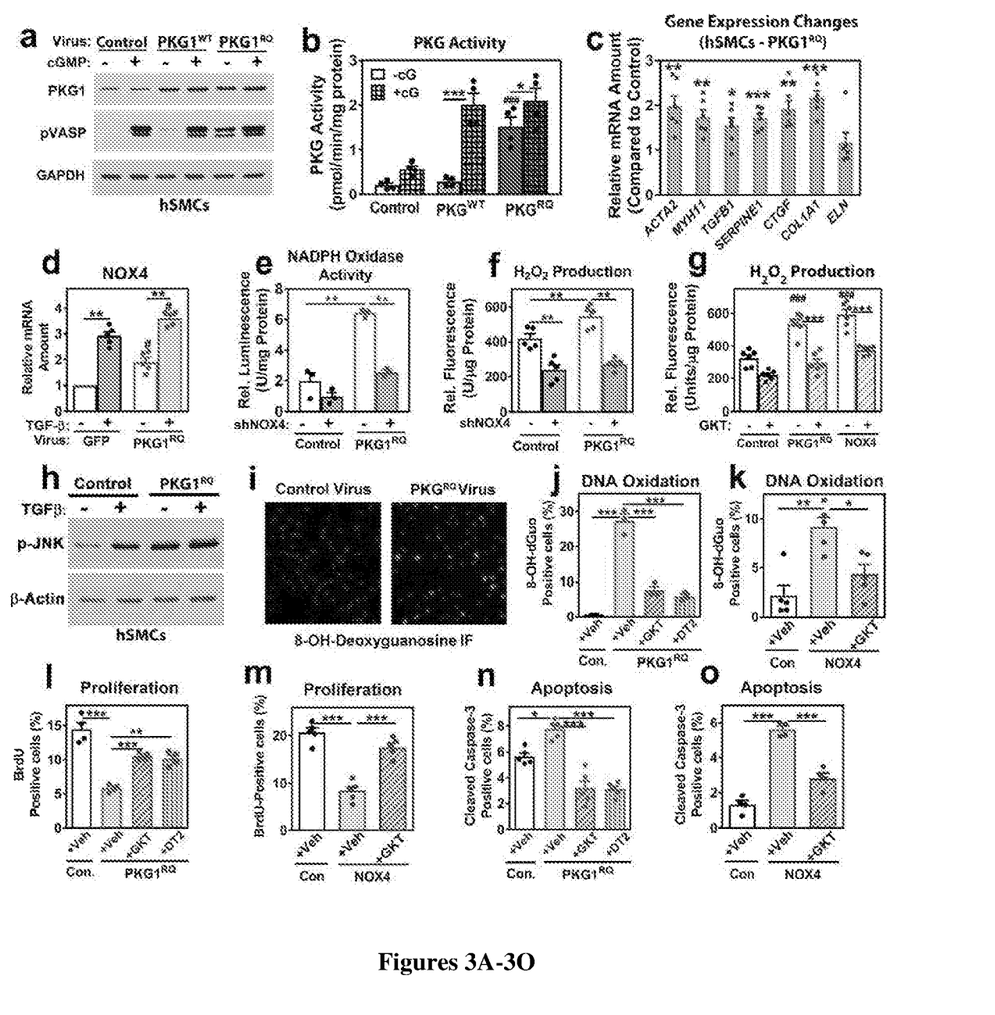
FIGS. 3A-3B show similar amounts of PKG1$^{WT}$ or PKG1$^{RQ}$ were expressed (FIG. 3A). PKG activity was assessed in the absence and presence of cGMP following endogenous VASP phosphorylation in cells (FIG. 3A) or using a synthetic peptide (FIG. 3B).
FIGS. 3C-3D show relative mRNA expression in SMCs expressing PKG1$^{RQ}$ was normalized to phosphoglycerokinase-1 mRNA and compared to cells infected with control virus; some cells (FIG. 3D) were treated with TGF-β for 24 h (gene names as in FIGS. 2A,2B).
FIGS. 3E-3F show NADPH oxidase activity and $H_2O_2$ production were measured in SMCs infected with control virus or virus encoding shRNA specific for NOX4.
FIG. 3G shows $H_2O_2$ production was measured in cells infected with virus encoding PKG1$^{RQ}$ or NOX4, and some cells were treated with the NOX1/4 inhibitor GKT137831 (GKT).
FIG. 3H shows JNK activation was assessed in SMCs treated with vehicle or TGF-β.
FIGS. 3I-3K show DNA oxidation was assessed by immunofluorescence staining for 8-OH-deoxyguanosine (FIG. 3I: pink nuclei; DNA was counterstained with Hoechst 33342). Some cells were treated with GKT137831 or with the PKG inhibitor DT2.
FIGS. 3L-3M show SMC proliferation was assessed by Br-deoxyuridine (BrdU) uptake into S-phase nuclei, with some cells treated with GKT137831 or DT2.
FIGS. 3N-3O show apoptosis was assessed by immunofluorescence staining for cleaved caspase-3 of cells cultured in 0.5% FBS. Graphs show means±SEM of three to six independent experiments. *p<0.05, p<0.01, *p<0.001 for the indicated comparisons; #p<0.05, ##p<0.01, #p<0.001 for the comparison between PKG1$^{RQ}$- or NOX4-expressing cells versus control cells under the same condition (FIG. 3C by one-sample t-test, FIGS. 3J-3O by one-way ANOVA, and FIGS. 3S and 3D-3G, by two-way ANOVA).

To study the mechanism whereby the mutant PKG1$^{RQ}$ leads to biochemical changes and changes in gene expression, the wild type and mutant enzyme were expressed in primary human aortic SMCs at levels 2-3 fold above endogenous PKG (FIG. 3A). Increased basal PKG activity was found in cells expressing the mutant enzyme-consistent with more of the mutant enzyme present than the endogenous enzyme; basal VASP phosphorylation was increased in PKG1$^{RQ}$-expressing cells, while cGMP-stimulated phosphorylation was similar in cells expressing wild type or mutant enzyme (FIGS. 3A,3B). Cells expressing PKG1$^{RQ}$ showed increased expression of contractile genes, and TGF-β1 and its target genes, including Nox4; expression of these genes was stimulated by TGF-β in both control cells and PKG$^{RQ}$-expressing cells (FIGS. 3C,3D). The PKG1$^{RQ}$-expressing cells produced more $H_2O_2$ than control cells or cells expressing wild type PKG1, and shRNA silencing of Nox4 reduced $H_2O_2$ production and NADPH oxidase activity to control levels; Nox2 shRNA had minimal effects (FIGS. 3E,3F). A NOX1/4 inhibitor (GKT137831)[35] reduced $H_2O_2$ production in the PKG1$^{RQ}$-expressing cells to a level found in control cells (FIG. 3G). These results indicate that NOX4 was the major source of excess $H_2O_2$ in cells expressing the mutant kinase. The PKG1$^{RQ}$-expressing cells also showed higher basal and TGF-β-induced JNK activation and DNA and protein oxidation than control cells, recapitulating findings in Prkg1$^{RQ/+}$ aortas (FIGS. 3H-3J). The PKG1$^{RQ}$-induced increase in DNA oxidation was largely prevented by DT2, indicating a requirement for PKG activity; the prooxidant effect of PKG1$^{RQ}$ was mimicked by Nox4 overexpression and blocked by GKT137831 (FIG. 3K).

PKG1$^{RQ}$ did not appear to regulate the Nox4 promoter via TGF-β, because PKG1$^{RQ}$-induced luciferase activity from a Nox4 promoter-luciferase reporter was not affected by an inhibitor of TGF-β receptor-1,[36] although the drug prevented promoter activation by TGF-β. However, stimulation of the Nox4 promoter required JNK activity and PKG1$^{RQ}$ enhanced the stimulatory effect of c-Jun on the promoter, suggesting that PKG1$^{RQ}$ stimulation of Nox4 transcription is mediated by JNK/cJun. Similarly, the oxysterol 7-ketocholesterol increases Nox4 transcription in human SMCs via activation of JNK/c-Jun.[37]

Expression of PKG1$^{RQ}$ in the human SMCs inhibited growth factor-induced proliferation and induced apoptosis, consistent with effects of NO/cGMP-induced PKG1 activation in rodent SMCs.[16, 17, 32, 38] The growth-inhibitory and pro-apoptotic effects of PKG1$^{RQ}$ were partly prevented by DT2 and GKT137831, and were mimicked by NOX4 overexpression, suggesting they were in part mediated by NOX4-induced oxidative stress (FIGS. 3I-3O). Phosphodiesterase-5 inhibitors such as sildenafil increase intracellular cGMP concentrations and activate PKG.[13] In the human aortic SMCs, sildenafil increased VASP phosphorylation and induced JNK activation when combined with low concentrations of an NO donor; the drug combination also inhibited SMC proliferation, thus mimicking some important effects of PKG1$^{RQ}$.

Figure 4A:
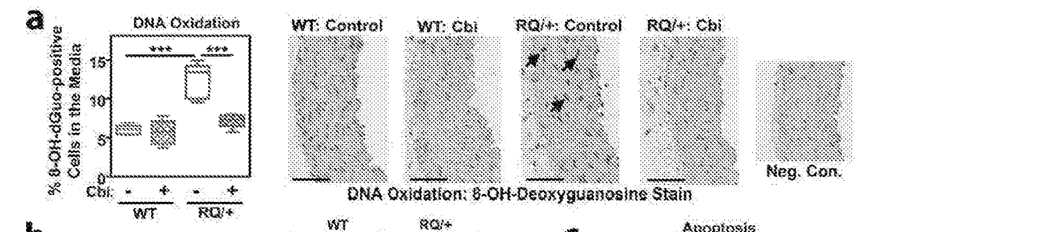
FIG. 4A shows DNA oxidation assessed by immunohistochemical staining with an antibody for 8-OH-deoxyguanosine; brown nuclei in the medial layer were counted (arrows show examples of cells counted as positive).
Figure 4B:
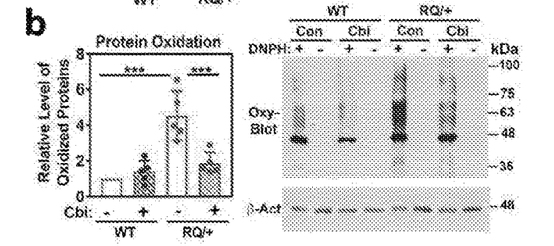
FIG. 4B shows protein carbonyl groups detected by OxyBlot™ in aortic extracts as described in FIG. 2G and quantified by densitometric scanning.
Figure 4C:
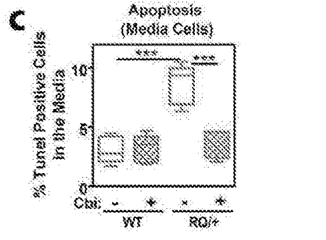
FIG. 4C shows SMC apoptosis assessed by TUNEL staining; only TUNEL-positive nuclei in the media were counted.
Figure 4D:
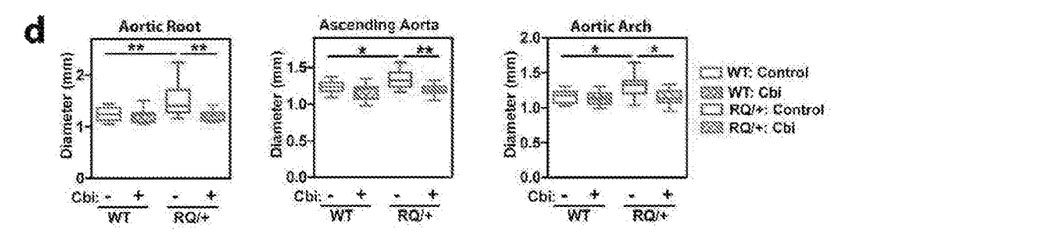
FIG. 4D shows diameter of the aortic root, ascending aorta, and aortic arch measured by ultrasound at the age of 12 months.
Figure 4E:
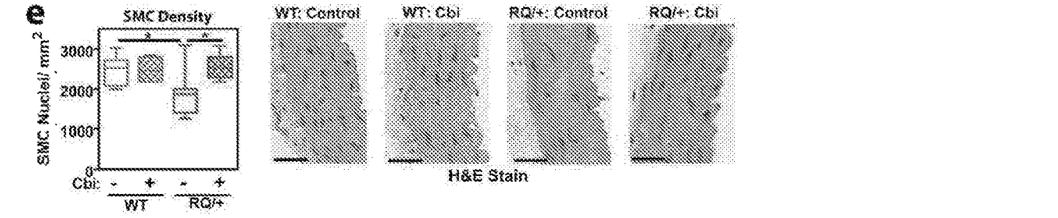
FIG. 4E shows SMC density measured by counting SMC nuclei on hematoxylin/eosin-stained sections.
Figure 4F:
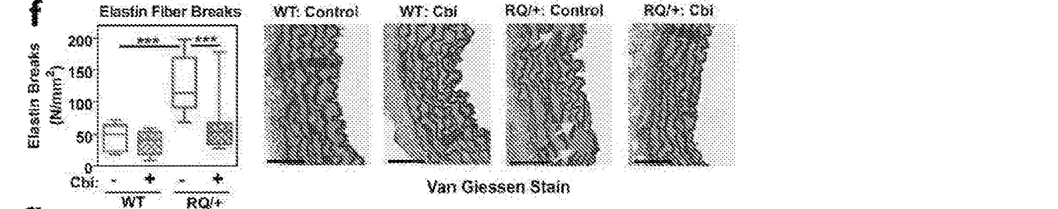
FIG. 4F shows elastin fiber breaks (arrows show examples) quantified on Van Giessen-stained cross-sections of the ascending aorta. Scale bars are 25 μm.

To determine if reducing reactive oxygen species could prevent the pathological changes that occur in the thoracic aortas of Prkg1$^{RQ/+}$ mice, mice were treated with cobinamide (Cbi), a vitamin $B_{12}$ analog that scavenges free radicals and exhibits potent anti-oxidant properties.[39] Providing Cbi in the drinking water from age 6 to 12 months reduced oxidative stress markers and SMC apoptosis in aortas of Prkg1$^{RQ/+}$ mice to values in WT mice (FIGS. 4A-4C). Notably, the Cbi completely prevented aortic dilation and SMC loss in the mutant mice, and reduced elastin fiber breaks and media collagen content to levels in WT mice (FIGS. 4D-4F). In human SMCs, Cbi decreased $H_2O_2$-induced JNK activation and protein oxidation, and it reduced protein oxidation in PKG1$^{RQ}$-expressing cells. Cbi had no effect on the activity of purified PKG1$^{RQ}$, nor did Cbi treatment of the mice affect PKG activity in aortic extracts. Thus, excess oxidative stress appears responsible for aortic disease caused by constitutive PKG1 activation.

Cbi had no significant effects in wild type mice, and no discernible toxicity, as judged by normal weight, clinical appearance, blood counts, and liver and kidney function tests. Cbi did not affect vitamin $B_{12}$-dependent functions, as indicated by normal serum homocysteine and methylmalonic acid concentrations in Cbi-treated mice.

Oxidative stress may activate PKG1 in a cGMP-independent fashion, presumably via Cys[43] oxidation, although the significance of PKG1 redox regulation in vivo is controversial.[40, 41] A small and similar amount of Cys[43]-oxidized, cross-linked PKG1 dimer was found in the aortas of wild type and Prkg1$^{RQ/+}$ mice, with no effect of Cbi on dimer amount. Treating human SMCs with high concentrations of $H_2O_2$ (i.e., 100-200 μM) induced Cys[43] oxidation of PKG1α, but it did not increase VASP phosphorylation, confirming the previous observation that Cys[43] oxidation does not activate the kinase.[41]

Figure 4G:
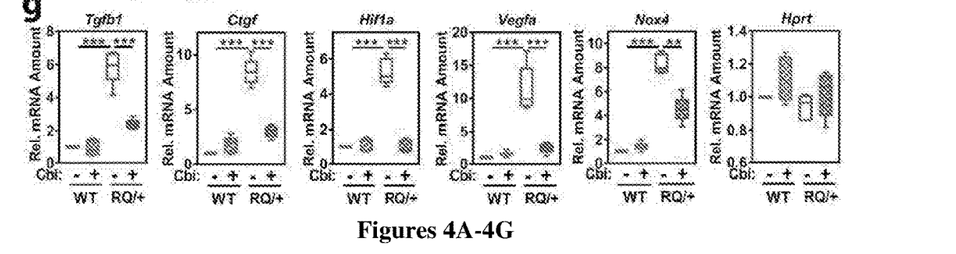
FIG. 4G shows mRNA expression in aortas of 12-month-old mice treated for 1 month with 1 mM Cbi in the drinking water (or left untreated, 5 female mice per group): TGF-β1 (Tgfb1); connective tissue growth factor (Ctgf); hypoxia-inducible factor-α (Hif1α); vascular endothelial growth factor-A (Vegfa); NADPH oxidase-4 (Nox4), and hypoxanthine phosphoribosyltransferase (Hprt). Genes were normalized to 18S rRNA and the mean ΔCt of WT mice was assigned a value of one. Boxplots show median and interquartile range with whiskers indicating the total range, and the graph in FIG. 4B shows means±SD (*p<0.05, p<0.01, and *p<0.001 for the indicated comparisons by two-way ANOVA).

Gene expression profiling in Nox4-transgenic and -knockout mice previously identified Tgfb1 and hypoxia-inducible factor-1α (Hif1a) as potential downstream targets of Nox4.[42-44] Increased expression of Nox4, Tgfb1 and its target Ctgf, was found and Hif1a and its target vascular endothelial growth factor A (Vegfa) in the aortas of 12 month-old Prkg1$^{RQ/+}$ mice compared to wild type litter mates (FIG. 4G). Cbi treatment of the mutant mice reduced all five transcripts, with Hif1a and Vegfa mRNAs reaching levels similar to those observed in wild type mice (FIG. 4G). Cbi suppression of Nox4 mRNA in the mutant mice may be explained by redox regulation of the Nox4 promoter.[45] Since dysregulation of the Hif-1α/Vegfa, and Tgfb1/Ctgf pathways has been linked to aortic aneurysm progression,[12, 28, 46, 47] these Nox4 target genes likely contribute to aortic pathology in PKG1$^{RQ/+}$ mice.

Figure 5A:
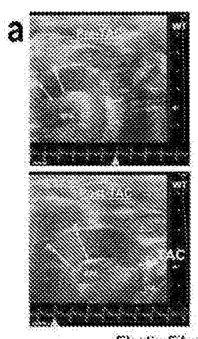
FIG. 5A shows an aortic arch by ultrasound imaging before and 2 weeks after TAC surgery in a wild type mouse (A=aortic root; B=ascending aorta; RPA, right pulmonary artery; LSA, left subclavian artery).
Figure 5B:
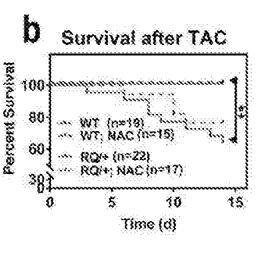
FIG. 5B shows survival of male wild type (WT) and PKG1$^{RQ/+}$ (RQ/+) mice after TAC (n=19 WT and n=22 RQ/+). Some animals received N-acetylcysteine (NAC) for four weeks before and 2 weeks after TAC, as indicated (n=15 WT and n=17 RQ/+). Only mice surviving 24 h after surgery were included, and surviving animals were euthanized 14 d after surgery. $p<0.01$ by log-rank (Mantel-Cox) test for the indicated comparison.
Figure 5C:
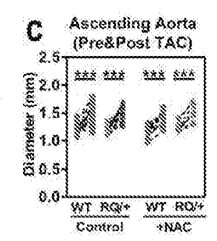
FIG. 5C shows the diameter of the ascending aorta before and 14 d after TAC, measured by ultrasound in surviving WT and Prkg1$^{RQ/+}$ mice (n as in FIG. 5A, *$p<0.001$ by 2-way ANOVA).
Figure 5D:
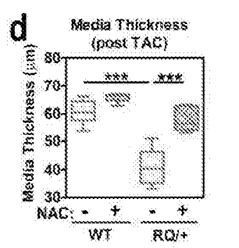
FIG. 5D shows media thickness measured on cross-sections of ascending aortas of surviving mice.
Figure 5E:
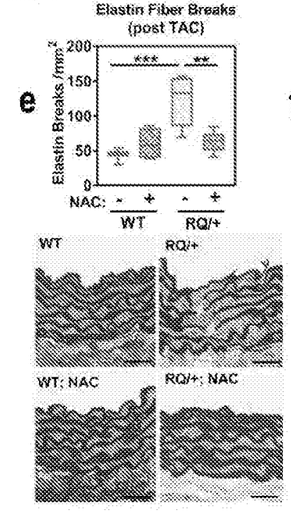
FIGS. 5E-5G show elastin fiber breaks, SMC density, and apoptosis of media cells assessed on ascending aorta cross-sections of mice euthanized 14 d after TAC surgery, as described in FIGS. 1F-1I (scale bars 25 μm; arrows show examples of elastin fiber breaks and some TUNEL-positive brown nuclei, respectively).
Figure 5F:
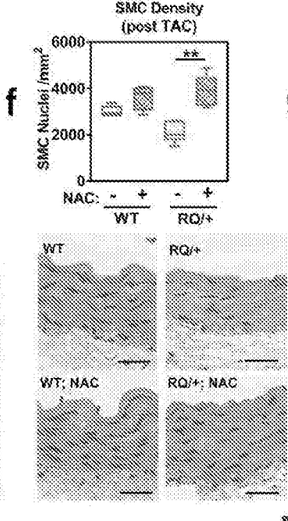
Figure 5G:
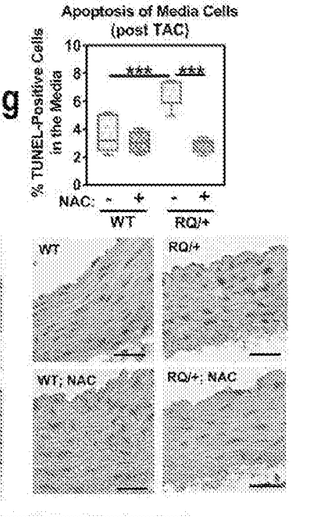
Figure 5H:
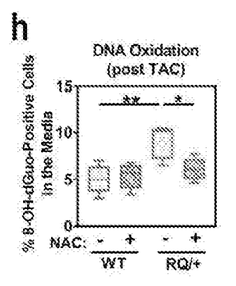
FIG. 5H shows DNA oxidation assessed by immunohistochemical staining for 8-OH-deoxyguanosine in nuclei of media cells, as described in FIG. 2D.
Figure 5I:
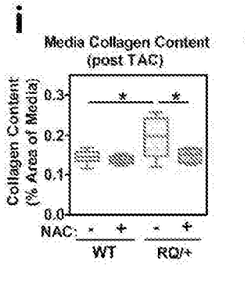
FIG. 5I shows media collagen content assessed on Masson-Trichrome stains as described in FIG. 1J. Boxplots in FIGS. 5D-5I show median and interquartile range with whiskers indicating the total range, for n=6 male mice per group; *$p<0.05$, $p<0.01$, *$p<0.001$ for the indicated comparisons by two-way ANOVA.

To determine if increased wall stress affected the aortas of young Prkg1$^{RQ/+}$ mice, 4-month-old mice were subjected to transverse aortic constriction (TAC),[48] which increased blood pressure in the ascending aorta in WT and Prkg1$^{RQ/+}$ similarly (FIG. 5A). Within two weeks of TAC, 36% of Prkg1$^{RQ/+}$ mice succumbed to aortic rupture—with hemothorax found on necropsies—while none of the WT mice died (FIG. 5B). Surviving mice of both genotypes showed similar pre-stenotic aortic dilation (FIG. 5C). TAC induced severe aortic wall pathology in young Prkg1$^{RQ/+}$ mice, with thinning of the media, elastin fiber breaks, loss of SMCs, increased SMC apoptosis, DNA oxidation, and media collagen content; none of these changes occurred in aortas from WT mice (FIGS. 5D-5I). To assess if oxidative stress contributed to the TAC-induced changes in the Prkg1$^{RQ/+}$ mutants, mice were treated with the antioxidant N-acetylcysteine (NAC) for four weeks prior to and two weeks after TAC. An antioxidant that was structurally- and mechanistically-unrelated to Cbi was purposely chosen. NAC treatment largely prevented TAC-induced aortic pathological changes, including media thinning, and reduced oxidative stress in Prkg1$^{RQ/+}$ mice, with no obvious effect in wild type mice (FIGS. 5D-5I). The NAC-treated mutant mice subjected to TAC showed a trend towards improved survival compared to untreated mice, but NAC did not affect pre-stenotic aortic dilation or aortic pressure gradients after TAC surgery.

Figure 5J:
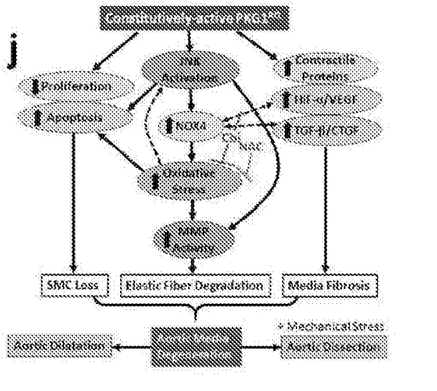

Several mechanisms whereby constitutive PKG1 activation induced thoracic aortic pathology were identified (FIG. 5J): (i) JNK is activated, up-regulating NOX4 and leading to increased oxidative stress, which further increases JNK activation; (ii) oxidative stress and JNK activation initiate SMC apoptosis and MMP-2 activation, causing elastin fiber degradation; (iii) impaired SMC proliferation and increased SMC apoptosis lead to SMC depletion; and (iv) increased TGF-β expression and target gene upregulation may contribute to aortic pathology, at least in late stages of aneurysm progression.[12, 28, 49] NOX4 upregulation leads to increased Hif-1α and Vegfa expression, and dysregulated HIF-1α/VEGF signalling has been observed in TAAD and linked to aortic aneurysm progression.[42-44, 46, 47, 50, 51]

In contrast to decreased SMC contractile proteins typically found in familial TAAD,[5, 8, 9, 52] PKG1$^{RQ}$-expressing SMCs showed an increase in contractile markers, consistent with the identified role of PKG1 in SMC phenotypic modulation.[14-17] Our data suggest that PKG1$^{RQ}$-expressing SMCs are "locked" in a low proliferative, contractile state, which interferes with vascular repair and aortic wall homeostasis. Increased reactive oxygen species and JNK activation leading to MMP upregulation have been implicated in several types of TAAD and abdominal aortic aneurysms.[10, 11, 31, 52-54] However, anti-oxidants and MMP inhibitors have had disappointing results in treatment of aortic aneurysms, which may be because of low systemic drug concentrations and/or low target affinities.[4, 55, 56] Cbi was highly effective in preventing age-related aortic pathology, including aortic dilation in the Prkg1$^{RQ/+}$ mice, and it reduced oxidative stress markers in the aorta. Cbi reacts very quickly with $O_2^-$ and has a favourable toxicity profile,[39] suggesting it could retard onset of other forms of TAAD associated with oxidative stress.[52, 53, 57] NAC was effective in ameliorating aortic wall injury after TAC, but its effect on mortality was limited, perhaps due to mechanical factors contributing to aortic rupture. Studies to confirm a role of NOX4 in aortic disease could be pursued by crossing Prkg1$^{RQ/+}$ mice with Nox4 knock-out mice; however, Nox4-deficient mice exhibit vascular abnormalities—including endothelial dysfunction and apoptosis—which would confound interpretation of results.[58, 59] Basal NOX4-derived $H_2O_2$ appears to have some vascular-protective effects, while increased NOX4 expression can exert both adverse and protective actions in cardiovascular disease models.[43, 60-62]

The data identify constitutive PKG1 activation as a cause of increased oxidative stress and vascular damage. The clinical significance of this finding reaches beyond the small number of people carrying the activating PRKG1, p.Arg177Gln mutation, because widespread use of PKG1-activating agents for a variety of disorders[3] may have unexpected long-term consequences on aortic wall homeostasis.

Methods

Generation of PKG1$^{RQ}$ Knock-in Mice. All animal experiments complied with ethical guidelines for the use of animals in research according to policies of the University of California, and were approved by the Institutional Care and Use Committee of the University of California, San Diego. Mice were housed in groups of 2-4 in a temperature-controlled environment with 12/12 h light/dark cycle. To generate PKG1$^{RQ}$ knock-in mice, KOD Xtreme Hotstart polymerase was used (EMD Millipore Corporation, Billerica, MA, USA) with 129S1 embryonic stem cell genomic DNA as a template to amplify prkg1 exon III, a 3.4-kb fragment of 5'-flanking sequence, and a 3.1-kb of 3'-flanking sequence. The arginine to glutamine mutation was generated in exon 3 by overlapping extension PCR using the primers originally used to amplify the 3' fragment, and mutagenesis primers. A targeting construct was assembled with the fragments on either side of a Frt-flanked neomycin cassette, and all PCR products were sequenced. The linearized construct was electroporated into 129S1 embryonic stem cells, and G418-resistant clones were screened by PCR. Homologous recombination was confirmed by Southern blot analysis of positive clones, using probes outside of the targeting construct. A positive clone with normal chromosome analysis in 20 metaphase spreads was injected into C57Bl/6 blastocysts to establish chimeric mice. Male chimeric mice were mated to C57BL/6J females and agouti pups were screened for the presence of the mutated allele. To remove the neomycin cassette, heterozygous mice were mated with flip recombinase-expressing mice in a 129S4 background (JAX mouse stock #003946). The removal of the neomycin cassette was confirmed, and subsequent genotyping was performed by PCR using tail DNA template. Additional screening was performed by restriction fragment length polymorphism; genomic DNA was PCR amplified with the primers and the 531 bp PCR product was digested with NciI. The wild type allele is cut into 188 bp and 343 bp fragments and the mutant allele remains uncut. To produce mice in an inbred 129S background, offspring from matings with 129S4 flip recombinase-expressing females were backcrossed for at least three generations with 129S1/SvImJ mice (JAX mouse stock #002448). These mice were used for all experiments, except in the TAC experiments shown in FIG. 5. Mice used for TAC experiments were backcrossed for at least eight generations into a C57BL/6NHsd background (Envigo catalog #044); this was done because cardiac outcomes after TAC have been well characterized in this background, and in male mice there is no evidence of heart failure 14 d after TAC.[48] Except for TAC, all experiments were performed with both male and female littermates from multiple litters, and results are shown for mixed gender, unless stated otherwise.

Randomization and Drug Treatment of Mice. At the time of weaning, male and female litter mates were separated and randomly assigned to new cages. At the age of 6 months (aging studies) or 10-14 weeks (TAC studies), matched cages containing mice born within a three week period were randomly assigned to treatment versus vehicle groups. For aging studies, some mice received 1 mM trihistidyl-cobinamine (Cbi) in the drinking water, starting from the age of 6 months until 12 months. For gene expression studies, mice were treated with 1 mM Cbi for one month only, from 11-12 months of age. For TAC studies, some mice received 1 mg/ml N-acetylcysteine (NAC) in the drinking water starting 4 weeks before until 2 weeks after the surgery. The drugs were dissolved freshly each week and filter-sterilized; fluid intake was monitored weekly. The Cbi dose was calculated to be 50 mg/kg/d, and the NAC dose was 500 mg/kg/d. Aquohydroxyl-cobinamide was synthesized from cobalamine by removal of the 5,6-dimethyl-benzimidazol ring; trihistidyl-cobinamide was obtained by adding three molar equivalents of L-histidine to the aquohydroxyl cobinamide.[63] Purity of the drug was >95% by high-pressure liquid chromatography.

Telemetry Blood Pressure Recordings. Blood pressures were measured on conscious 4-month-old mice using a telemetry blood pressure recording system (Data Sciences International, Ponemah, PA-C10 pressure transmitter). Mice were anesthetized with isoflurane (1.5%), and a 20-25 mm midline incision was made vertically at the ventral throat area. The PAC-10 transmitter catheter was introduced into left carotid artery and the tip was advanced into the thoracic aorta. Data were recorded for three days, after a two-week post-operative recovery period.

Transthoracic Echocardiography. Prior to echocardiography, a depilatory cream was applied to the anterior chest wall to remove hair. Mice were anesthetized with 5% isoflurane for 15 seconds and then maintained at 0.5% throughout the echocardiography examination. Small needle electrodes for simultaneous electrocardiogram were inserted into one upper and one lower limb. Transthoracic echocardiography was performed using the FUJIFILM VisualSonics Inc., Vevo 2100 high-resolution ultrasound system with a linear transducer of 32-55 MHz. Measurements of aortic diameters were recorded during end-diastole at the aortic root, ascending aorta, and aortic arch; they were performed by a single, highly experienced operator, who was blinded to genotype and treatment of the mice. Bland Altman analyses were performed to determine inter- and intra-observer variability of echo measurements. Measuring the diameter of the ascending aorta, the average of the differences between two observers was −0.061 mm (with 95% limits of agreement between −0.18 and 0.06 mm), and the average of differences between two observations by the same observer were 0.024 mm (with 95% limits of agreement between −0.12 and 0.17 mm).

Arterial Ring Isometric Tension Measurements. Isometric tension in aortas was measured as previously described,[64] with minor modifications. Thoracic aortas were dissected in Krebs-Henseleit solution, cleaned of any adherent connective tissue, and cut into 1.5-2 mm segments. Rings with intact endothelium were mounted in a wire myograph over 40 µm wires, set at a resting tension of 0.5 g, and allowed to equilibrate at 37° C. for 45 min with intermittent washes every 15 min. After equilibration, aortas were treated with 40 mM K$^+$-solution. For vascular relaxation by acetylcholine (Sigma) or 8-(4-chlorophenylthio)cGMP (8-CPT-cGMP, BioLog), each aortic ring was pre-contracted to generate ~0.15 g contraction by treatment with prostaglandin-F2α (PGF$_{2α}$ 2-8 µM, Thermo-Fisher). The degree of relaxation was calculated as a percent of PGF$_{2α}$-induced contraction.

PKG1 Purification and Activity Assays. Wild type and mutant PKG1$^{RQ}$ were expressed with N-terminal FLAG epitope tags in transiently-transfected 293T cells (ATCC, CRL3216), purified with anti-FLAG beads and eluted with FLAG peptide, and kinase activity assays were performed.[41] Kinase activity in SMC and aortic extracts was measured using an optimized peptide in the presence of 1.25 µM protein kinase inhibitor peptide (PKI) to inhibit cAMP-dependent protein kinase.[65] Assays were performed with [γ-$^{32}$PO$_4$]ATP (1.3 Ci/mmol; 50 µM) in the presence and absence of 3 µM cGMP, and were linear with time and protein concentration. In some assays, the PKG-specific inhibitory peptide DT2 was included at 10 µM.

Western Blotting. Following anesthesia with ketamine (100 mg/kg) and xylazine (10 mg/kg) by intraperitoneal injection, mice were exsanguinated and perfused with ice-cold phosphate-buffered saline (PBS) containing protease inhibitor cocktail (Calbiochem #539131). Aortas were excised, cleaned from surrounding tissue, and snap-frozen in liquid nitrogen within 15 min of euthanasia. Frozen aortas were pulverized and sonicated (3×10 sec) in ice-cold RIPA buffer (50 mM NaCl, 50 mM Tris-HCl, pH 8, 1% NP-40, 0.1% SDS, 0.5% sodium deoxycholate) supplemented with 1 mM NaF, 1 mM β-glycerolphosphate, and protease inhibitor cocktail. Western blots were developed with primary antibodies specific for PKG1 (1:1000, Cell Signaling Technology; 3248, VASP-phospho-Ser$^{259}$ (1:1000, Cell Signaling Technology; 3114), GAPDH (1:1000, Cell Signaling Technology; 2118), β-actin (1:5000, Santa Cruz Biotechnology; 47778), and JNK-phospho-Thr$^{183}$/Tyr$^{185}$ (1:1000, Cell Signaling Technology; 9251). Blots were developed and visualized with enhanced chemiluminescence using LI-COR Odyssey (with ImageStudio, V5) or with film in the linear range of exposure (with densitometry scanning using ImageJ (V1.51). Protein carbonyl groups (aldehydes and ketones) were detected using the OxyBlot™ Protein Oxidation Detection Kit (Millipore EMD; S7150). Unprocessed scans of blots are provided in the Source Data file.

Histomorphometric Studies. Following anesthesia with i.p. ketamine (100 mg/kg) and xylazine (10 mg/kg), mice were perfusion-fixed with 10 ml of 4% paraformaldehyde for 3 min under physiological pressure. Thoracic aortas were excised and further fixed overnight. Paraffin-embedded ascending aortas were cross-sectioned into 5 µm thick sections, which were stained with haematoxylin and eosin (to count SMC nuclei), Van Gieson elastin stain (to detect elastin fiber breaks) and Masson's Trichrome stain (to quantify collagen), following standard protocols. Slides were scanned with a Hamamatsu NanoZoomer 2.0 HT System and analyzed using Digital Pathology NDP.view2 software. The images were captured at 10×, 40× and 80× magnification for histomorphometric analyses.[66] The thickness of the aortic media was measured using a straight-line tool at four different points (at 0, 90, 180, 270 degrees) on two different sections, and the mean was reported. SMC nuclei and elastin fiber breaks were counted manually at 40× magnification, on five non-overlapping areas of aortic media measuring 0.025 µm$^2$ each; means were calculated and expressed per mm$^2$. Collagen content of the media area was measured at 10× magnification on Masson's Trichrome-stained cross-sections using Image-Pro Premier software (V 9.0, Media Cybernetics). Histomorphometric measurements were confirmed by an investigator who was blinded to the genotype and treatment group of the mice.

Immunohistochemical Staining of Aortic Sections. Terminal deoxynucleotidyl transferase-mediated dUTP-biotin nick end-labeling (TUNEL) staining of deparaffinized aortic sections was performed using the Apoptag Peroxidase In-situ Apoptosis Detection Kit (Millipore EMD; S7100) according to the manufacturer's instructions. For 8-OH-dGuo staining of deparaffinized sections, antigen retrieval was done by placing slides into boiling 10 mM sodium citrate buffer, pH 6, and letting them cool for 30 minutes. The sections were treated with RNase A (100 µg/ml) in 10 mM Tris HCl, pH 7.5, 1 mM EDTA, 0.4 M NaCl at 37° C. for 1 h, rinsed, treated with proteinase K (10 µg/ml) in phosphate-buffered saline (PBS) at room temperature for 7 min, and permeabilized with 0.2% TritonX100 for 15 min. Samples were blocked in 2% BSA/PBS, and incubated in anti-8-OH-dGuo (1:50 dilution in 1% BSA/PBS), followed by a goat anti-mouse horseradish peroxidase-coupled secondary antibody (1:100, Jackson Immunoresearch). Slides were developed using 3,3-diaminobenzidine substrate (Vector Laboratories) and counterstained with methyl green.

Dihydroethidium Staining of Aortas. Ascending aortas were dissected, and immediately immersed in 10 µM dihydroethidium (Life Technologies; C10422) solution in PBS and incubated for 30 min at 37° C. The tissue was rinsed 4× in PBS, placed in Tissue-Tek OCT compound (Miles Laboratories), and snap-frozen in liquid nitrogen. Cryosections were fixed in 4% paraformaldehyde for 15 minutes at room temperature, washed in PBS, and counterstained in Hoechst 33342; sections were imaged within 4 h by fluorescence microscopy.

Quantitative RT-PCR. Aortas were dissected and snap-frozen as described above; they were pulverized and immersed in Trizol (Molecular Res. Center, TR118). Total RNA was isolated, reverse-transcribed using iScript cDNA synthesis kit (Bio-Rad), and PCR was performed using a MX3005P real-time PCR detection system with Brilliant II SYBR Green Mix (Agilent Technologies) as described.[67] All primers were intron-spanning (except for 18S rRNA), and were tested with serial cDNA dilutions. Relative changes in mRNA expression were analyzed using the comparative $2^{-\Delta\Delta Ct}$ method, with 18S rRNA and phosphoglycerate kinase-1 serving as internal controls.[68]

SMC Culture and Adenovirus Infection. Murine aortic SMCs were isolated from the aortas of 8-12 week old wild type and PKG1$^{RQ/+}$ mice and were cultured in Smooth Muscle Basal Media (SmBM) containing 20% FBS, pyruvate, HEPES, L-glutamine, penicillin/streptomycin and growth factors (SmBM Bullet kit; CC-4149 from Lonza), as previously described.[69] Two independent cell isolates from wild type and PKG1$^{RQ}$ mice were used at passage one. Human primary aortic SMCs were purchased from Lifeline Cell Technology (Frederick, MD, FC-0015) and cultured in VascuLife Basal Medium supplemented with recombinant epidermal growth factor, insulin, and fibroblast growth factor-b, ascorbic acid, L-glutamine, 20% FBS, gentamycin, and amphotericin (Vasculife SMC LifeFactors kit; LS-1040 from Lifeline Technologies). Human SMCs were used at passages 3-6. Adenovirus was generated using the ViraPower Adenoviral Expression System (Thermo Fisher).[67] Human SMCs were infected with virus expressing wild type or mutant human PKG1α (containing the R177Q mutation); the MOI was 3-10 and titrated to produce wild type and mutant kinase at 2-3 fold the level of endogenous PKG1 at 72 h post infection. For Nox4 over-expression, human SMCs were infected with virus expressing murine Nox4 to increase $H_2O_2$ production to a level comparable to that induced by PKG1$^{RQ}$. For knock-down of NOX2 and NOX4, SMCs were infected with adenovirus expressing shNOX2 or shNOX4 oligomers (downstream of the U6 promoter) at an MOI of 100; $H_2O_2$ production and NADPH oxidase activity assays were performed 48 h later (as described below).

Nox4 Promoter Activity Assay. A 1707 bp fragment of the Nox4 promoter region 5' to the translational start site was cloned from mouse genomic DNA using KOD Hot Start DNA Polymerase (Millipore) and primers. The PCR product was inserted into pGL3 (Promega) using XhoI and NcoI sites, and sequenced. C3H/10T1/2 cells (ATCC, CCL226) were transfected with lipofecamine 2000, and luciferase activity was measured using a single vial luminometer.[15]

SMC Immunofluorescence Staining. SMCs were cultured on glass coverslips and fixed in 4% paraformaldehyde. For 8-hydroxydeoxyguanosine (8-OH-dGuo) staining, cells were treated with RNase A and proteinase K as described above for tissue sections. Cells were permeabilized with 0.2% TritonX100 in PBS and blocked with 2% BSA in PBS (8 min and 1 h, respectively, at room temperature). Cells were incubated with the anti-8-OH-dGuo antibody (1:100, Abeam, ab26842) in 1% BSA in PBS overnight at 4° C. Apoptotic cells were stained with anti-cleaved caspase-3 antibody (1:100, Cell Signaling Technology #9664) in 1% BSA in PBS overnight at 4° C. To label cells in S-phase, cells were incubated with 200 µM 8-Br-deoxyuridine (BrdU, Sigma) for 48 h, fixed in paraformaldehyde and permeabilized with 0.2% TritonX100 as above. After rinsing with PBS, cells were incubated with DNAse I (Sigma) for 30 min at 37° C. and blocked with 2% BSA in PBS for 1 h, prior to incubation with anti-BrdU antibody (1:200, Sigma) for 1 h at room temperature. After washing in PBS, cells were incubated with a Texas Red-conjugated secondary antibody (1:100, Jackson Immunoresearch), and nuclei were counterstained with Hoechst 33342 (Thermo-Fischer Scientific). Images were analyzed with a Keyence BZ-X700 fluorescence microscope.

Amplex Red and NADPH Oxidase Assays. Primary murine SMCs isolated from wild type or PKG1$^{RQ/+}$ aortas, and human SMCs infected with control, wild type, or mutant PKG1$^{RQ}$ virus, were seeded at 4×10$^4$ cells/well in 96-well plates, and $H_2O_2$ production was measured using an Amplex Red/Hydrogen Peroxide/Peroxidase Assay Kit (Thermo Fischer Scientific). Cells were incubated 16 h later in 0.1 mL of reaction mixture containing 50 µM Amplex Red and 0.1 units/mL horseradish peroxidase. Fluorescence was measured every min in a BioTek Synergy 2 plate reader, using 540 nm excitation and 590 nm emission wavelengths.

To measure NADPH oxidase activity by lucigenin-enhanced chemiluminescence, SMCs were homogenized in PBS with 1 mM EDTA and protease inhibitor cocktail (Calbiochem #539131), and supernatants were obtained after centrifugation at 750 g for 5 min. The lucigenin assay was performed in 50 mM phosphate buffer, pH 7.0, 1 mM EGTA, 150 mM sucrose, with 5 µM lucigenin, and was started by the addition of 100 µM NADPH.[52] Photon emission was measured every second for 5 min in a luminometer, and activity (after subtraction of a buffer blank) was expressed as relative luminescence units per mg protein.

NOX2 and NOX4 shRNAs were expressed from adenoviral vectors. Amplex Red and NADPH oxidase activity assays were performed 48 h after infection of human SMCs.

Thiobarbituric Acid-reactive Substances Assay. Frozen aortas were pulverized and lysed in 0.15 mL ice-cold RIPA buffer and sonicated three times for 10 sec. To 0.1 mL of the tissue lysate, 0.2 mL 10% trichloroacetic acid and 0.3 mL 0.67% thiobarbituric acid were added, and samples were boiled for 45 min. The thiobarbituric acid adducts were extracted in butanol and measured using 515 and 553 nm as excitation and emission wavelengths, respectively. Malondialdehyde standards were from Cayman Chemical.

Ascobyl Radical Measurement by Electron Paramagnetic Resonance. Murine blood samples were obtained by cardiac puncture at the time of euthanasia, and serum samples were kept frozen at −80° C. for up to 4 weeks prior to analysis. EPR spectra were recorded at room temperature using a MiniScope MS400 spectrometer (Magnatech).[3, 12] EPR conditions were: modulation amplitude, 0.2 mT; sweep time, 20 s; sweep rate, 1/s. Peak amplitude was measured in arbitrary units.

Matrix Metalloproteinase Activity Assays. Frozen aortas were pulverized and lysed in 10 mM sodium cacodylate, 150 mM NaCl, 10 mM $CaCl_2$), 1 mM $ZnCl_2$, 1% TritonX100, 0.1% SDS, 0.5% sodium deoxycholate, 0.02% sodium azide, and 2% DMSO. For zymography, 6 μg of extract protein were subjected to SDS-polyacrylamide gel electrophoresis under non-reducing conditions in gels containing 1% gelatin.[16] Gels were washed three times in 2.5% TritonX100 for 30 min at room temperature, and incubated in 50 mM Tris HCl, pH 7.5, 10 mM $CaCl_2$), 200 mM NaCl and 1 μM $ZnCl_2$ for 18-36 h at 37° C. Gels were stained with Coomassie Blue and destained until clear bands showed zones of gelatinolytic activity. Culture supernatant from MDA-MB231 breast cancer cells served as a positive control. Total MMP activity in extracts of aortic arches was also measured with a fluorescently-labeled elastin peptide, using the Fluorimetric Sensolyte 520 Generic MMP assay kit (Anaspec; AS-71158) according to the manufacturer's instructions, in the linear range of the assay. Results were confirmed using a MMP Activity Assay Kit from Abcam (ab112146) based on a FRET peptide as MMP activity indicator.

Transverse Aortic Constriction. The TAC procedure was performed on 14-20-week-old wild type and $PKG1^{RQ/+}$ mice by a single, highly experienced operator, who was blinded to genotype and treatment of the mice.[48] Mice were anesthetized with ketamine (50 mg/kg) and xylazine (5 mg/kg) by intraperitoneal injection and then received isoflurane (0.75-1.5%) for complete induction of anesthesia. Mice were ventilated with a pressure ventilator. The chest cavity was entered in the second intercostal space at the left upper sternal border and the transverse aorta was isolated between the carotid arteries. Aortic constriction was performed by tying a 7-0 silk suture ligature against a 27-27.5-gauge needle (according to the body weight), and the needle was promptly removed to yield a constriction of about 0.4 mm in diameter. Following the constriction procedure, the chest was closed with 6-0 silk sutures. Buprenorphine (0.1 mg/kg, 100 μl/mouse) was given 15-30 minutes prior to anticipated recovery, and every 12 h for three days postoperatively. Mice were euthanized 14 d after the procedure. Mice dying within 24 h after TAC surgery were excluded from analyses: 6/40 wild type and 5/44 heterozygous mice died for a total peri-operative mortality of 13%.

Blood Pressure Gradient Measurements Post TAC. To evaluate the stress level generated by TAC, the pressure gradient between the two carotid arteries was measured at the end of the study (day 14). Anesthesia was induced, and mice were ventilated as described for TAC. Both carotid arteries were exposed and cannulated with stretched PE 50 catheters connected to fluid-filled transducers. Both carotid artery pressures were simultaneously recorded and analyzed in LabChart (ADInstruments).

Statistics. Most data are presented as dot plots with means±SD or box- and whiskers plots, where the upper and lower margins of the box define the $75^{th}$ and $25^{th}$ percentiles, respectively, the internal line defines the median, and the whiskers show the total range. Bar graphs showing means±SEM were used for data normalized to a control group (e.g., qRT-PCR results, where the control group was assigned a value of one) and for FIG. 3, showing averages of at least three independent cell culture experiments. Where appropriate (for n>7), the data were tested for normality using the D'Agostino-Pearson omnibus normality test, and for equal variance using an F test (to compare the variances of two groups), or the Browne and Forsythe test (for 3 or more groups). For comparison of two groups, P values refer to unpaired, 2-tailed Student's t test. For multiple comparisons, P values refer to either 1-way ANOVA followed by Sidak's multiple comparison test, or to 2-way ANOVA with Holm-Sidak's multiple comparison test (e.g., when determining how the genotype of the mice affected response to drug treatment or TAC). $P<0.05$ was considered statistically significant. When the assumptions of normal distribution and/or equal variances were not met, a non-parametric test was chosen (Mann-Whitney test for two groups and Kruskal-Wallis test for three or more groups). Data analysis was performed using GraphPad Prism 7 software.

REFERENCES

1. Guo, D. C., et al. Recurrent gain-of-function mutation in PRKG1 causes thoracic aortic aneurysms and acute aortic dissections. *Am J Hum Genet* 93, 398-404 (2013).
2. Gago-Diaz, M., et al. PRKG1 and genetic diagnosis of early-onset thoracic aortic disease. *Eur J Clin Invest* 46, 787-794 (2016).
3. Buglioni, A. & Burnett, J. C., Jr. New Pharmacological Strategies to Increase cGMP. *Annu Rev Med* 67, 229-243 (2016).
4. Davis, F. M., Rateri, D. L. & Daugherty, A. Mechanisms of aortic aneurysm formation: translating preclinical studies into clinical therapies. *Heart* 100, 1498-1505 (2014).
5. Verstraeten, A., Luyckx, I. & Loeys, B. Aetiology and management of hereditary aortopathy. *Nat Rev Cardiol* 14, 197-208 (2017).
6. Milewicz, D. M., Prakash, S. K. & Ramirez, F. Therapeutics Targeting Drivers of Thoracic Aortic Aneurysms and Acute Aortic Dissections: Insights from Predisposing Genes and Mouse Models. *Annu Rev Med* 68, 51-67 (2017).
7. Pinard, A., Jones, G. T. & Milewicz, D. M. Genetics of Thoracic and Abdominal Aortic Diseases. *Circ Res* 124, 588-606 (2019).
8. Ailawadi, G., et al. Smooth muscle phenotypic modulation is an early event in aortic aneurysms. *J Thorac Cardiovasc Surg* 138, 1392-1399 (2009).
9. Inamoto, S., et al. TGFBR2 mutations alter smooth muscle cell phenotype and predispose to thoracic aortic aneurysms and dissections. *Cardiovasc Res* 88, 520-529 (2010).
10. Holm, T. M., et al. Noncanonical TGFbeta signaling contributes to aortic aneurysm progression in Marfan syndrome mice. *Science* 332, 358-361 (2011).
11. Xiong, W., Meisinger, T., Knispel, R., Worth, J. M. & Baxter, B. T. MMP-2 regulates Erkl/2 phosphorylation and aortic dilatation in Marfan syndrome. *Circ Res* 110, e92-e101 (2012).

12. Cook, J. R., et al. Dimorphic effects of transforming growth factor-beta signaling during aortic aneurysm progression in mice suggest a combinatorial therapy for Marfan syndrome. *Arterioscler Thromb Vasc Biol* 35, 911-917 (2015).
13. Francis, S. H., Busch, J. L., Corbin, J. D. & Sibley, D. cGMP-dependent protein kinases and cGMP phosphodiesterases in nitric oxide and cGMP action. *Pharmacol Rev* 62, 525-563 (2010).
14. Lincoln, T. M., Wu, X., Sellak, H., Dey, N. & Choi, C. S. Regulation of vascular smooth muscle cell phenotype by cyclic GMP and cyclic GMP-dependent protein kinase. *Front Biosci* 11, 356-367 (2006).
15. Zhang, T., et al. A cysteine-rich LIM-only protein mediates regulation of smooth muscle-specific gene expression by cGMP-dependent protein kinase. *J Biol Chem* 282, 33367-33380 (2007).
16. Schwappacher, R., et al. A molecular mechanism for therapeutic effects of cGMP-elevating agents in pulmonary arterial hypertension. *J Biol Chem* 288, 16557-16566 (2013).
17. Sinnaeve, P., et al. Soluble guanylate cyclase alpha(1) and beta(1) gene transfer increases NO responsiveness and reduces neointima formation after balloon injury in rats via antiproliferative and antimigratory effects. *Circ Res* 88, 103-109 (2001).
18. Oller, J., et al. Nitric oxide mediates aortic disease in mice deficient in the metalloprotease Adamts1 and in a mouse model of Marfan syndrome. *Nat Med* 23, 200-212 (2017).
19. Lameijer, C. M., Tielliu, I. F., van Driel, M. F. & Zeebregts, C. J. Type B aortic dissection after the use of tadalafil. *Ann Thorac Surg* 93, 651-653 (2012).
20. Famularo, G., Polchi, S., Di Bona, G. & Manzara, C. Acute aortic dissection after cocaine and sildenafil abuse. *J Emerg Med* 21, 78-79 (2001).
21. Nachtnebel, A., Stollberger, C., Ehrlich, M. & Finsterer, J. Aortic dissection after sildenafil-induced erection. *South Med J* 99, 1151-1152 (2006).
22. Croft, A. P., Nader, K. & Arulanantham, N. A very unusual headache. *Clin Med (Lond)* 14, 58-60 (2014).
23. Goudie, A. R., Lipworth, B. J., Hopkinson, P. J., Wei, L. & Struthers, A. D. Tadalafil in patients with chronic obstructive pulmonary disease: a randomised, double-blind, parallel-group, placebo-controlled trial. *Lancet Respir Med* 2, 293-300 (2014).
24. Dostmann, W. R., et al. Highly specific, membrane-permeant peptide blockers of cGMP-dependent protein kinase Ialpha inhibit NO-induced cerebral dilation. *Proc Natl Acad Sci USA* 97, 14772-14777 (2000).
25. Chung, A. W., et al. Endothelial dysfunction and compromised eNOS/Akt signaling in the thoracic aorta during the progression of Marfan syndrome. *Br J Pharmacol* 150, 1075-1083 (2007).
26. Neptune, E. R., et al. Dysregulation of TGF-beta activation contributes to pathogenesis in Marfan syndrome. *Nat Genet* 33, 407-411 (2003).
27. Gallo, E. M., et al. Angiotensin II-dependent TGF-beta signaling contributes to Loeys-Dietz syndrome vascular pathogenesis. *J Clin Invest* 124, 448-460 (2014).
28. Daugherty, A., Chen, Z., Sawada, H., Rateri, D. L. & Sheppard, M. B. Transforming Growth Factor-beta in Thoracic Aortic Aneurysms: Good, Bad, or Irrelevant? *J Am Heart Assoc* 6(2017).
29. Drummond, G. R., Selemidis, S., Griendling, K. K. & Sobey, C. G. Combating oxidative stress in vascular disease: NADPH oxidases as therapeutic targets. *Nat Rev Drug Discov* 10, 453-471 (2011).
30. Shen, H. M. & Liu, Z. G. JNK signaling pathway is a key modulator in cell death mediated by reactive oxygen and nitrogen species. *Free Radic Biol Med* 40, 928-939 (2006).
31. Yoshimura, K., et al. Regression of abdominal aortic aneurysm by inhibition of c-Jun N-terminal kinase. *Nat Med* 11, 1330-1338 (2005).
32. Soh, J. W., et al. Protein kinase G activates the JNK1 pathway via phosphorylation of MEKK1. *J Biol Chem* 276, 16406-16410 (2001).
33. Kamata, H., et al. Reactive oxygen species promote TNFalpha-induced death and sustained JNK activation by inhibiting MAP kinase phosphatases. *Cell* 120, 649-661 (2005).
34. Komalavilas, P., Shah, P. K., Jo, H. & Lincoln, T. M. Activation of mitogen-activated protein kinase pathways by cyclic GMP and cyclic GMP-dependent protein kinase in contractile vascular smooth muscle cells. *J Biol Chem* 274, 34301-34309 (1999).
35. Teixeira, G., et al. Therapeutic potential of NADPH oxidase 1/4 inhibitors. *Br J Pharmacol* 174, 1647-1669 (2017).
36. Vogt, J., Traynor, R. & Sapkota, G. P. The specificities of small molecule inhibitors of the TGFss and BMP pathways. *Cell Signal* 23, 1831-1842 (2011).
37. Pedruzzi, E., et al. NAD(P)H oxidase Nox-4 mediates 7-ketocholesterol-induced endoplasmic reticulum stress and apoptosis in human aortic smooth muscle cells. *Mol Cell Biol* 24, 10703-10717 (2004).
38. Chiche, J. D., et al. Adenovirus-mediated gene transfer of cGMP-dependent protein kinase increases the sensitivity of cultured vascular smooth muscle cells to the antiproliferative and pro-apoptotic effects of nitric oxide/cGMP. *J Biol Chem* 273, 34263-34271 (1998).
39. Jiang, J., et al. Hydrogen Sulfide—Mechanisms of Toxicity and Development of an Antidote. *Sci Rep* 6, 20831 (2016).
40. Prysyazhna, O., Rudyk, O. & Eaton, P. Single atom substitution in mouse protein kinase G eliminates oxidant sensing to cause hypertension. *Nat Med* 18, 286-290 (2012).
41. Kalyanaraman, H., Zhuang, S., Pilz, R. B. & Casteel, D. E. The activity of cGMP-dependent protein kinase Ialpha is not directly regulated by oxidation-induced disulfide formation at cysteine 43. *J Biol Chem* 292, 8262-8268 (2017).
42. You, Y. H., Quach, T., Saito, R., Pham, J. & Sharma, K. Metabolomics Reveals a Key Role for Fumarate in Mediating the Effects of NADPH Oxidase 4 in Diabetic Kidney Disease. *J Am Soc Nephrol* 27, 466-481 (2016).
43. Zhang, M., et al. NADPH oxidase-4 mediates protection against chronic load-induced stress in mouse hearts by enhancing angiogenesis. *Proc Natl Acad Sci USA* 107, 18121-18126 (2010).
44. Matsushima, S., et al. Broad suppression of NADPH oxidase activity exacerbates ischemia/reperfusion injury through inadvertent downregulation of hypoxia-inducible factor-1alpha and upregulation of peroxisome proliferator-activated receptor-alpha. *Circ Res* 112, 1135-1149 (2013).
45. Lassegue, B., San Martin, A. & Griendling, K. K. Biochemistry, physiology, and pathophysiology of NADPH oxidases in the cardiovascular system. *Circ Res* 110, 1364-1390 (2012).

46. Wang, W., et al. Hypoxia-inducible factor 1 in clinical and experimental aortic aneurysm disease. *J Vasc Surg* 68, 1538-1550 e1532 (2018).
47. Li, X., et al. Curcumin attenuates the development of thoracic aortic aneurysm by inhibiting VEGF expression and inflammation. *Mol Med Rep* 16, 4455-4462 (2017).
48. Moore-Morris, T., et al. Resident fibroblast lineages mediate pressure overload-induced cardiac fibrosis. *J Clin Invest* 124, 2921-2934 (2014).
49. Liu, X. H., et al. NADPH oxidase 4 contributes to connective tissue growth factor expression through Smad3-dependent signaling pathway. *Free Radic Biol Med* 94, 174-184 (2016).
50. Oshima, Y., Tanimoto, T., Yuji, K. & Tojo, A. Association Between Aortic Dissection and Systemic Exposure of Vascular Endothelial Growth Factor Pathway Inhibitors in the Japanese Adverse Drug Event Report Database. Circulation 135, 815-817 (2017).
51. Del Porto, F., et al. The multitasking role of macrophages in Stanford type A acute aortic dissection. Cardiology 127, 123-129 (2014).
52. Chen, J., et al. Loss of Smooth Muscle alpha-Actin Leads to NF-kappaB-Dependent Increased Sensitivity to Angiotensin II in Smooth Muscle Cells and Aortic Enlargement. *Circ Res* 120, 1903-1915 (2017).
53. Yang, H. H., van Breemen, C. & Chung, A. W. Vasomotor dysfunction in the thoracic aorta of Marfan syndrome is associated with accumulation of oxidative stress. *Vascul Pharmacol* 52, 37-45 (2010).
54. Jimenez-Altayo, F., et al. Redox stress in Marfan syndrome: Dissecting the role of the NADPH oxidase NOX4 in aortic aneurysm. *Free Radic Biol Med* 118, 44-58 (2018).
55. McCormick, M. L., Gavrila, D. & Weintraub, N. L. Role of oxidative stress in the pathogenesis of abdominal aortic aneurysms. *Arterioscler Thromb Vasc Biol* 27, 461-469 (2007).
56. Raaz, U., et al. Hemodynamic regulation of reactive oxygen species: implications for vascular diseases. *Antioxid Redox Signal* 20, 914-928 (2014).
57. Ejiri, J., et al. Oxidative stress in the pathogenesis of thoracic aortic aneurysm: protective role of statin and angiotensin II type 1 receptor blocker. *Cardiovasc Res* 59, 988-996 (2003).
58. Di Marco, E., et al. NOX4-derived reactive oxygen species limit fibrosis and inhibit proliferation of vascular smooth muscle cells in diabetic atherosclerosis. *Free Radic Biol Med* 97, 556-567 (2016).
59. Schroder, K., et al. Nox4 is a protective reactive oxygen species generating vascular NADPH oxidase. *Circ Res* 110, 1217-1225 (2012).
60. Fulton, D. J. & Barman, S. A. Clarity on the Isoform-Specific Roles of NADPH Oxidases and NADPH Oxidase-4 in Atherosclerosis. *Arterioscler Thromb Vasc Biol* 36, 579-581 (2016).
61. Touyz, R. M. & Montezano, A. C. Vascular Nox4: a multifarious NADPH oxidase. *Circ Res* 110, 1159-1161 (2012).
62. Kuroda, J., et al. NADPH oxidase 4 (Nox4) is a major source of oxidative stress in the failing heart. *Proc Natl Acad Sci USA* 107, 15565-15570 (2010).
63. Chan, A., et al. Nitrocobinamide, a new cyanide antidote that can be administered by intramuscular injection. *J Med Chem* 58, 1750-1759 (2015).
64. Han, Y., et al. SGLT inhibitors attenuate NO-dependent vascular relaxation in the pulmonary artery but not in the coronary artery. *Am J Physiol Lung Cell Mol Physiol* 309, L1027-1036 (2015).
65. Dostmann, W. R., et al. Delineation of selective cyclic GMP-dependent protein kinase Ialpha substrate and inhibitor peptides based on combinatorial peptide libraries on paper. *Pharmacol Ther* 82, 373-387 (1999).
66. Kuang, S. Q., et al. FOXE3 mutations predispose to thoracic aortic aneurysms and dissections. *J Clin Invest* 126, 948-961 (2016).
67. Kalyanaraman, H., et al. Nongenomic thyroid hormone signaling occurs through a plasma membrane-localized receptor. *Sci Signal* 7, ra48 (2014).

What is claimed is:

1. A method of treating a non-atherosclerotic aortic disease in a subject comprising administering to a subject in need an effective amount of cobinamide, a cobinamide derivative, or a salt thereof.

2. The method of claim 1, wherein the non-atherosclerotic aortic disease is aortic aneurysm, aortic dissection, or aortic dilation.

3. The method of claim 1, wherein the non-atherosclerotic aortic disease is due to Marfan syndrome or thoracic aortic aneurysms and dissections (TAAD).

4. The method of claim 1, wherein a cobalt atom of the cobinamide, cobinamide derivative, or salt thereof independently is coordinated with one or more ligands.

5. The method of claim 1, wherein the cobinamide, cobinamide derivative, or salt thereof is administered orally.

6. A method of treating non-atherosclerotic aortic disease comprising administering to a subject in need an effective amount of a composition comprising an anti-oxidant to lower reactive oxygen species.

7. The method of claim 6, wherein the anti-oxidant is cobinamide, a cobinamide derivative, or a salt thereof.

8. The method of claim 6, wherein the method inhibits aortic dilation and SMC loss.

9. The method of claim 6, wherein the method inhibits elastin fiber breaks.

10. The method of claim 6, wherein the method inhibits $H_2O_2$-induced JNK activation and protein oxidation.

11. The method of claim 6, wherein the method down-regulates Hif-1α/Vegfa or Tgfb1/Ctgf pathways.

12. The method of claim 6, wherein the method inhibits PKG activity.

* * * * *